(12) United States Patent
Zhou et al.

(10) Patent No.: US 8,597,634 B2
(45) Date of Patent: *Dec. 3, 2013

(54) INTERFERON ALPHA-2A MODIFIED BY POLYETHYLENE GLYCOL AND METHODS OF PREPARATION THEREOF

(75) Inventors: Weidong Zhou, Xia men (CN); Qingjiang Xiao, Xia men (CN); Li Sun, Xia men (CN); Tiebing Wang, Xia men (CN); Bin Liu, Xia men (CN); Song Lin, Xia men (CN); Min Liu, Xia men (CN); Fenghong Yin, Xia men (CN); Lu Zhuang, Xia men (CN); Lifang Lei, Xia men (CN)

(73) Assignee: Biosteed Gene Expression Tech. Co., Ltd., Fuijan (CN)

( * ) Notice: Subject to any disclaimer, the term of this patent is extended or adjusted under 35 U.S.C. 154(b) by 77 days.

This patent is subject to a terminal disclaimer.

(21) Appl. No.: 12/676,511

(22) PCT Filed: Sep. 4, 2007

(86) PCT No.: PCT/CN2007/002643
§ 371 (c)(1),
(2), (4) Date: May 27, 2010

(87) PCT Pub. No.: WO2009/030065
PCT Pub. Date: Mar. 12, 2009

(65) Prior Publication Data
US 2010/0239532 A1    Sep. 23, 2010

(51) Int. Cl.
*A61K 38/21* (2006.01)
*A61K 38/00* (2006.01)
*A61K 39/385* (2006.01)
*C07K 14/56* (2006.01)

(52) U.S. Cl.
USPC ......... 424/85.7; 424/194.1; 530/351; 514/1.1

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 5,382,657 A | 1/1995 | Karasiewicz | |
| 5,762,923 A * | 6/1998 | Gross et al. | 424/85.7 |
| 6,042,822 A * | 3/2000 | Gilbert et al. | 424/85.7 |
| 6,610,830 B1 * | 8/2003 | Goeddel et al. | 530/351 |
| 2002/0172661 A1 * | 11/2002 | Shirley et al. | 424/85.6 |
| 2004/0223950 A1 * | 11/2004 | Brugger et al. | 424/85.7 |
| 2005/0180946 A1 * | 8/2005 | Ji et al. | 424/78.38 |
| 2006/0223145 A1 * | 10/2006 | Lohray et al. | 435/69.5 |
| 2011/0158943 A1 | 6/2011 | Zhou et al. | |

FOREIGN PATENT DOCUMENTS

| | | |
|---|---|---|
| CN | 1243779 | 3/2006 |
| EP | 0809996 | 12/1997 |
| EP | 0593868 | 4/1998 |
| WO | WO03/076490 | 9/2003 |
| WO | WO2009/030065 | 3/2009 |
| WO | WO2009/030066 | 3/2009 |

OTHER PUBLICATIONS

UniProtKB Accession No. Q86UP4 (Jun. 1, 2003).*
Chamow et al., "Modification of CD4 Immunoadhesin with Monomethoxypoly(ethylene glycol) Aldehyde via Reductive Alkylation," Bioconjugate Chemistry. vol. 5, No. 2 pp. 133-140 (1994).
Delgado et al., "The Uses and Properties of PEG-Linked Proteins," Critical Reviews in Therapeutic Drug Carrier Systems. vol. 9 pp. 249-304 (1992).
Grace et al., "Structural and Biologic Characterization of Pegylated Recombinant IFN-α2b," Journal of Interferon and Cytokine Research. vol. 21, No. 12 pp. 1103-1115 (2001).
Henco et al., "Structural relationship of human interferon alpha genes and pseudogenes," J. Mol. Biol. vol. 185 pp. 227-260 (1985).
Inoue et al., "A highly enhanced thrombopoietic activity by polyethylene glycol-modified recombinant human interleukin-6," J. Lab. Clin. Med. vol. 124 pp. 529-536 (1994).
International Preliminary Report on Patentability corresponding to International Patent Application No. PCT/CN2007/002643 dated Mar. 9, 2010.
International Preliminary Report on Patentability corresponding to International Patent Application No. PCT/CN2007/002644 dated Mar. 9, 2010.
International Search Report corresponding to International Patent Application No. PCT/CN2007/002643 mailed on Jun. 12, 2008.
International Search Report corresponding to International Patent Application No. PCT/CN2007/002644 mailed on Jun. 12, 2008.
Katre et al., "Chemical modification of recombinant interleukin 2 by polyethylene glycol increases its potency in the murine Meth A sarcoma model," PNAS. vol. 84 pp. 1487-1491 (1987).
Katre, "The conjugation of proteins with polyethylene glycol and other polymers: Altering properties of proteins to enhance their therapeutic potential," Advanced Drug Delivery Reviews. vol. 10 pp. 91-114 (1993).
Monfardini et al., "A Branched Monomethoxypoly(ethylene glycol) for Protein Modification," Bioconjugate Chem. vol. 6, No. 1 pp. 62-69 (1995).
Official Action corresponding to U.S. Appl. No. 12/676,525 dated May 3, 2011.
Oritani et al., "Type I interferons and limitin: a comparison of structures, receptors, and functions," Cytokine and Growth Factor Reviews. vol. 12 pp. 337-348 (2001).
Satake-Ishikawa et al., "Chemical Modification of Recombinant Human Granulocyte Colony-Stimulating Factor by Polyethylene Glycol Increases its Biological Activity in vivo," Cell Structure and Function. vol. 17 pp. 157-160 (1992).

(Continued)

*Primary Examiner* — Robert Landsman
*Assistant Examiner* — Bruce D Hissong
(74) *Attorney, Agent, or Firm* — Jenkins, Wilson, Taylor & Hunt, P.A.

(57) ABSTRACT

The present invention relates to interferon (IFN)-α2a modified at a specific Lys residue with Y-shaped branched polyethylene glycol (PEG) derivative and the preparation thereof, as well as the use of the prepared IFN-α2a modified by PEG at a single amino acid residue in medicines.

28 Claims, 7 Drawing Sheets

(56) References Cited

OTHER PUBLICATIONS

Tsutsumi et al., "Chemical Modification of Natural Human Necrosis Factor-α with Polyethylene Glycol Increases Its Anti-tumor Potency," Jpn. J. Cancer Research. vol. 85 pp. 9-12 (1994).

Wang et al, "Identification of the Major Positional Isomer of Pegylated Interferon Alpha-2b," Biochemistry. vol. 39, No. 35 pp. 10634-10640 (2000).

Wang et al., "Structural and biological characterization of pegylated recombinant interferon alpha-2b and its therapeutic implications," Advanced Drug Delivery Reviews. vol. 54 pp. 547-570 (2002).

Official Action corresponding to U.S. Appl. No. 12/676,525 dated Sep. 15, 2011.

Official Action corresponding to U.S. Appl. No. 12/676,525 dated Jul. 27, 2012.

Official Action corresponding to U.S. Appl. No. 12/676,525 dated May 23, 2013.

\* cited by examiner

INTERFERON ALPHA-2A MODIFIED BY POLYETHYLENE GLYCOL AND METHODS OF PREPARATION THEREOF

FIELD OF THE INVENTION

The present invention relates to interferon α-2a modified by Y-shaped branched polyethylene glycol (PEG) at a single amino acid residue and the preparation thereof, as well as the use of the prepared PEGylated IFN-α2a at a single amino acid residue in pharmaceutical field.

BACKGROUND OF THE INVENTION

Interferons (IFNs) are a family of small molecule proteins or glycoproteins produced by eukaryotic cells in response to viral infection and other antigenic stimuli, which display broad-spectrum antiviral, antiproliferative and immunomodulatory effects. IFNs have been widely applied in the treatment of various conditions and diseases, such as viral infections, e.g. hepatitis B, hepatitis C and HIV; inflammatory disorders and diseases, e.g. multiple sclerosis, arthritis, asthma, cystic fibrosis and interstitial lung disease; and tumors e.g. myelomas, lymphomas, liver cancer, lung cancer, hairy-cell leukemia, and so on (Kenji Oritani, Paul W Kincade, et al. Type I interferon and limitin: a comparison of structures, receptors, and functions. Cytokine and Growth Factor Reviews, 12, 337-348, 2001; Yu-Sen Wang, Stephen Youngster, et al. Structural and biological characterization of PEGylated recombinant interferon alpha-2b and its therapeutic implications. Advance Drug Delivery Reviews, 54, 547-570, 2002).

IFNs are classified into four types according to their differences in chemical, immunological, and biological properties: interferon-α, β, γ and ε. Interferon-α (IFN-α) is secreted by leukocytes. Human IFNs-α are encoded by a multigene family consisting of about 20 genes, the encoded proteins sharing up to about 90% amino acid sequence homology (Henco K., Brosius F. J., et al. J. Mol. Biol., 185, 227-260, 1985). Human IFN-α2a is one of the subtypes of the α2 subfamily of human IFN-α family, and is a single chain protein with various biological activities. The single chain protein consists of 165 amino acid residues, as shown in SEQ ID No.1, in which the N-terminal amino acid is Cys with one free α-$NH_2$ group, and the residues in positions 23, 31, 49, 70, 83, 112, 121, 131, 133, 134 and 164 of the amino acid sequence are Lys, each of which contains one free ε-$NH_2$ group.

IFNs are usually administered parenterally in clinical treatments. The short in vivo half-life (2-4 h) and strong immunogenicity of IFNs result in a shorter dosing interval and a higher dosing frequency. As the generated antibodies significantly decrease the therapeutic efficacy, it is difficult to achieve ideal clinical efficacy. The polyethylene glycol (PEG) modification technology developed in recent years has provided a possible solution to the above problems.

PEG is an inert, nontoxic and biodegradable organic polymer, and is important in the fields of both biotechnology and pharmaceutics. PEG modification technique is to link PEG to an active protein via covalent bond. After the PEGylation, the properties of the protein can be significantly improved, e.g. the prolongation of drug metabolic half-life, the reduction of immunogenicity, the increase of safety, the improvement of therapeutic efficacy, the decrease of dosing frequency, the increase of drug solubility/water solubility, the increase of resistance against proteolysis, the facilitation of drug controlled release and so on. For further details please refer to Inada et al. J. Bioact. and Compatible Polymers, 5, 343, 1990, Delgado et al. Critical Reviews in Therapeutic Drug Carrier Systems, 9, 249, 1992, Katre. Advanced Drug Delivery Systems, 10, 91, 1993, and U.S. patent publication U.S. Pat. No. 4,179,337.

It is disclosed in U.S. Pat. No. 4,179,337, after linking PEG to an enzyme or insulin, the immunogenicity of the protein was reduced, while simultaneously the activities of the protein were reduced as well. This was also found in G-CSF (Satake-Ishikawa et al. Cell Structure and Function, 17, 157-160, 1992), IL-2 (Katre et al. Proc. Natl. Acad. Sci. USA, 84, 1487, 1987), TNF-α (Tsutsumi et al. Jpn. J. Cancer Res., 85, 9, 1994), IL-6 (Inoue et al. J. Lab. Clin. Med., 124, 529, 1994) and CD4-IgG (Chamow et al. Bioconj. Chem., 5, 133, 1994).

Currently many kinds of PEGylated proteins have been applied clinically. In 1990, the PEGylated-bovine adenosine deaminase (Adagen) produced by ENZON Inc. was approved by FDA, and used to treat severe combined immunodeficiency disease (pegfamg013102LB). In 1994, another PEG-modified protein for treating acute lymphoblastic leukemia, the PEGylated asparaginase (pegaspargase, Oncaspar), was also marketed in US (103411s5052lbl). The PEG modified interferon-α2b (PEG IFN-α2b, PEG-Intron) developed by Schering-Plough was approved by FDA for marketing in 2000 and the PEGylated interferon-α (PEG IFN-α2a, Pegasys) produced by Hoffman-la Roche Ltd. was also approved for marketing in 2002, both of which are used to treat hepatitis (103964s5037lbl, pegsche011901LB). In 2002, the PEG modified human granulocyte colony-stimulating factor produced by Amgen Inc. (PEG-filgrastim, Neulasta) was also approved by FDA, which is used to treat metastatic breast cancer (pegfamg013102LB). The FDA also accepted the application for PEGylated human growth factor antagonist developed by Pharmacia. The PEG combined TNF-α antibody fragment from Celltech and the PEG-TNF receptor from Amgen are tested in the advanced clinical trials. The first PEG-organic molecule conjugate, PEGylated camptothecin, has also entered phase II of clinical trial. In 2004, the PEG modified oligonucleotide (Pegaptanib, Macugen™) was approved by FDA. The in vivo metabolism of the PEG in the drug (or PEG itself) has already been clearly understood, and PEG has been proven to be a good and safe drug modifier without any adverse effect.

Generally, a PEG molecule modifies a protein by linking itself to the N-terminal α-amino group or ε-amino group of an internal Lys residue in the protein molecule. There are normally three types of PEGs for protein modification: a linear chain molecule (EP 0593868), an U-shaped branched molecule (EP 0809996) and an Y-shaped branched molecule (CN1243779C). Up to now, there are still no reports about the preparation of Y-shaped branched PEG-modified IFN-α2a and the separation of different IFNs-α2a with a single PEG molecule modification at different amino acid positions. It was reported that the branched PEG-modified protein displayed better pH tolerance, thermo-stability and resistance against proteolysis than linear chain PEG-modified proteins (Monfardini et al. Bioconjugate Chem., 6, 62, 1995).

The PEGs that can be linked to a protein drug normally need to derivatized, so that one or two terminal groups of the ends of PEGs can be chemically activated to possess a proper functional group which displays activity, and thus can form a stable covalent bond with, at least one functional group of the drug to be linked. For example, PEGs can be linked to ε-$NH_2$ of a Lys residue within the protein peptide chain, or to α-$NH_2$ of the N-terminal amino acid residue of the protein peptide chain. In the PEGylation of IFN-α described in European patent EP0809996, PEG-NHS is linked through nucleophilic substitution to α-NH₂ of the N-terminal amino acid or ε-NH₂ of Lys in IFN-α. The PEG-NHS mentioned in the above patent is a U-shaped branched PEG derivative (PEG₂-NHS), the molecular formula thereof as below:

wherein, R and R' are independently a low molecular weight alkyl group, n and n' are from 600 to 1500, and the average molecular weight of the PEGs is from 26 KD to 66 KD. The molecular formula of the PEG₂-NHS-modified IFN-α is as below:

Where one or more PEG₂-NHS molecules are linked to α-NH₂ of the N-terminal amino acid or ε-NH₂ of Lys in IFN-α, the obtained products are a mixture of non-PEGylated IFN-α, PEGylated IFNs-α at a single amino acid residue, and PEGylated IFNs-α at multiple amino acid residues. The PEGylated IFN-α at a single amino acid residue can be isolated from the obtained products by an appropriate purification means. IFN-α has one N-terminal amino acid and more than one Lys residues, namely several reactive sites for PEG₂-NHS, so the isolated PEGylated IFNs-α at a single amino acid residue are a mixture of the isomers of the PEGylated IFNs-α at different single amino acid residues.

In European patent EP 0593868, linear-chain PEG is used to modify IFN, the molecular formula of the modified product as below:

wherein R is a low molecular weight alkyl group; $R_1$, $R_2$, $R_3$ and $R_4$ are H or low molecular weight alkyl groups; m is from 1 to the number of possible PEG modification positions in IFN; W is O or NH; x is from 1 to 1000, y and z are from 0 to 1000, x+y+z is from 3 to 1000; and at least one of $R_1$, $R_2$, $R_3$ and $R_4$ is a low molecular weight alkyl group, Yu-Sen Wang et al (Yu-Sen Wang et al, Advanced Drug Delivery Reviews, 54:

547-570, 2002. Yu-Sen Wang et al, Biochemistry, 39, 10634-10640, 2000.) have reported the modification of rIFN-α2b with 12 KD linear monomethoxy-PEG (Peg-Intron) and shown that the products analyzed by HPLC-IE are a mixture of more than 14 isomers modified by PEG at different single amino acid residues. The molecular formula of the linear PEG used by Yu-Sen Wang et al is shown below:

wherein the average molecular weight of the PEG is 12 KD.

SUMMARY OF THE INVENTION

The PEG derivatives used in the present invention are novel branched, Y-shaped branched PEG derivatives, and their structures are different from those of the U-shaped branched PEGs. The biggest difference between these two kinds of PEGs is that: two-branch PEG chains of the Y-shaped PEG derivatives according to the present invention are connected together through N atom, while the two-branch PEG chains of the U-shaped PEG derivatives in EP0809996 are connected together through C atom. The molecular composition of the Y-shaped PEG derivatives according to the present invention is shown as below:

wherein, $P_a$ and $P_b$ are same or different PEGs; j is an integer from 1 to 12; $R_i$ is H, a substituted or unsubstituted C1-C12 alkyl group, a substituted aryl, an aralkyl or a heteroalkyl; $X_1$ and $X_2$ are independently linking groups, wherein $X_1$ is $(CH_2)_n$, and $X_2$ is selected from the group consisting of $(CH_2)_n$, $(CH_2)_nOCO$, $(CH_2)_nNHCO$, and $(CH_2)_nCO$; n is an integer from 1 to 10; and F is a terminal group selected from the group consisting of a hydroxyl group, a carboxyl group, an ester group, acyl chloride, hydrazide, maleimide, pyridine disulfide, capable of reacting with an amino group, a hydroxyl group or a mercapto group of a therapeutic agent or a substrate to form covalent bond. In one preferred embodiment of the present invention, the Y-shaped PEG derivative molecule is shown as below:

wherein, R and R' are independently a C1-C4 alkyl group, preferably methyl; m and m' denote the degree of polymerization and can be any integer; m+m' is preferably from 600 to 1500; $R_i$ is H, a substituted or unsubstituted C1-C12 alkyl, a substituted aryl, an aralkyl, or a heteroalkyl group; j is an integer from 1 to 12; and F is a terminal group selected from the group consisting of a hydroxyl group, a carboxyl group, an ester group, carboxylic acid chloride, hydrazide, maleimide, pyridine disulfide, capable of reacting with an amino group, a hydroxyl group or a mercapto group of a therapeutic agent or a substrate to form a covalent bond. Preferably, the average total molecular weight of the PEG is from about 10000 to about 60000 Dalton, most preferably about 40000 Dalton.

In one preferred embodiment of the present invention, a possible structural formula of the Y-shaped PEG derivative molecule is shown as formula (I):

wherein R and R' are independently a C1-C4 alkyl group, preferably methyl; m and m' denote the degree of polymerization and can be any integer; m+m' is preferably from 600 to 1500; j is an integer from 1 to 12; and the average total molecular weight of the PEG is about 40000 Dalton.

The present inventors used Y-shaped branched PEG derivatives (YPEG) to modify interferon-α2a (IFN-α2a), and isolated the YPEG-IFNs-α2a, modified by YPEG at a single amino acid residue, by Q-Sepharose FF ion-exchange chromatography. Moreover, the isolated YPEG-IFNs-α2a modified at a single amino acid residue were further separated by SP-Sepharose FF chromatography to obtain YPEG-IFN-α2a wherein the YPEG is principally linked to the side chain ε-NH$_2$ of Lys at position 134 in SEQ ID NO.1, which is called YPEG-IFN-α2a(134). After measurement, it is found that the in vitro activity of the YPEG-IFN-α2a(134) is significantly higher than that of the YPEG-IFN-α2a in which the YPEG is linked to another amino acid position, and the half-life of the YPEG-IFN-α2a(134) in serum is significantly longer than that of the unmodified IFN-α2a.

Therefore, the present invention provides PEGylated IFNs-α2a at a single amino acid residue, the structure of which is as below:

wherein $P_a$ and $P_b$ are same or different PEGs; j is an integer from 1 to 12; $R_i$ is H, a substituted or unsubstituted C1-C12 alkyl group, a substituted aryl, an aralkyl, or a heteroalkyl group; $X_1$ and $X_2$ are independently linking groups, wherein $X_1$ is $(CH_2)_n$, and $X_2$ is selected from the group consisting of $(CH_2)_n$, $(CH_2)_nOCO$, $(CH_2)_nNHCO$ and $(CH_2)_nCO$, wherein n is an integer from 1 to 10.

In one preferred embodiment of the present invention, the structural formula of the PEGylated IFN-α2a of the present invention is as below:

(II)

wherein R and R' are independently a C1-C4 alkyl group, preferably methyl; j is an integer from 1 to 12; m and m' denote the degree of polymerization and can be any same or different integers; m+m' is preferably from 600 to 1500. In this structure, a Y-shaped branched PEG molecule is linked to an IFN-α2a molecule via one single amino acid residue. The average molecular weight of the YPEG-IFNs-α2a in formula (II) depends principally on the degree of polymerization, m and m'. Where m+m' is preferably from 600 to 1500, the corresponding average molecular weight of the YPEG is from about 26000 to about 66000 Dalton. Where m+m' is preferably from 795 to 1030, the corresponding average molecular weight of the YPEG is from about 35000 to about 45000 Dalton. Where m+m' is preferably from 885 to 1030, the corresponding average molecular weight of the YPEG is from about 39000 to about 45000 Dalton. Where m+m' is most preferably 910, the corresponding average molecular weight of the YPEG is 40000 Dalton. The ratio of m and m' can be in a range from 0.5 to 1.5, preferably from 0.8 to 1.2.

In one preferred embodiment, in the PEGylated IFN-α2a of the present invention, a PEG molecule is linked to IFN-α2a via an amido bond formed by α-amino group of the N-terminal amino acid or the side chain ε-amino group of Lys residue of IFN-α2a corresponding to position 23, 31, 49, 70, 83, 112, 121, 131, 133, 134, or 164 as shown in SEQ ID No.1.

In a further preferred embodiment, in the PEGylated IFN-α2a of the present invention, a PEG molecule is linked to IFN-α2a via an amido bond principally formed by the side chain ε-amino group of Lys residue of IFN-α2a corresponding to position 134 as shown in SEQ ID No. 1.

Optionally, the IFN-α2a of the present invention can be extracted from natural sources or obtained by the recombinant biotechnology. Preferably, the IFN-α2a is human IFN-α2a (hIFN-α2a) having the amino acid sequence of SEQ ID No.1, which is extracted from natural sources or obtained by the recombinant biotechnology. More preferably, the human IFN-α2a is recombinant human IFN-α2a (rhIFN-α2a). The rhIFN-α2a can be artificially synthesized, or be expressed from prokaryotic expression systems such as *E. coli*, or be expressed from eukaryotic yeast expression systems such as *Pichia*, or be expressed from insect cell expression systems or mammalian cell expression systems such as CHO. The preparation methods of the natural or recombinant IFN-α2a and the activity tests of IFN-α2a and YPEG modified IFN-α2a are known in prior art.

Similar to IFN-α2a, the YPEG-IFN-α2a of the present invention can also be used clinically to treat tumors and viral infections, such as hepatitis, hairy-cell leukemia, cell-mediated lympholysis, Kaposi's sarcoma and so on. In clinical, the

YPEG-IFN-α2a of the present invention is clearly improved, as compared to IFN-α2a, in stability, solubility, half-life in serum and clinical therapeutic efficacy. For the mode of administration, the YPEG-IFN-α2a of the present invention can be administered to the patients in the form of a composition comprising a pharmaceutically effective amount of the YPEG-IFN-β2a and a pharmaceutically acceptable carrier or excipient. Hence, the present invention, in another aspect, also provides a composition comprising a pharmaceutically effective amount of the PEGylated IFN-α2a of the present invention and a pharmaceutically acceptable carrier or excipient. Preferably, the composition comprises mannitol, an amino acid, sodium chloride and sodium acetate, wherein the amino acid is preferably selected from the group consisting of aspartic acid, asparagine and glycine.

In another aspect, the present invention also provides the use of the PEGylated IFN-α2a of the invention or the composition comprising the PEGylated IFN-α2a of the invention in the preparation of a medicament for treating a disease in need of IFN-α2a treatment. Preferably, the disease in need of IFN-α2a treatment is selected from the group consisting of viral infections e.g. hepatitis B, hepatitis C, hepatitis D and condyloma acuminatum, tumors e.g. hairy-cell leukemia, chronic myeloid leukemia, low-grade malignant non Hodgkin's leukemia, cell-mediated lympholysis, Kaposi's sarcoma, multiple myeloma, malignant melanoma, cutaneous T-cell lymphoma, laryngeal papilloma, recurrent or metastatic renal cell carcinoma, inflammatory disorders and diseases e.g. multiple sclerosis, arthritis, asthma, cystic fibrosis and interstitial lung disease, and myeloproliferative diseases related thrombocythemia.

In order to obtain the YPEG modified IFN-α2a, in one embodiment of the present invention, initially the PEG moiety of activated YPEG derivatives such as PEG N-hydroxyl succinimidyl ester (YPEG-NHS) is covalently linked to an amino (—NH$_2$) group of the protein through nucleophilic substitution, wherein the amino group includes N-terminal α-amino group and an ε-amino group of Lys residue of the protein. The reaction equation for the generation of YPEG-IFN-α2a from IFN-α2a and YPEG is as below:

modified at multiple amino acid residues (YPEG$_n$-IFN-α2a), wherein the products modified at a single amino acid residue can be the predominant products by adjusting the reaction condition.

Subsequently, the YPEG-IFNs-α2a, modified by PEG at a single amino acid residue, can be isolated from the mixture of all kinds of the YPEG modified IFNs-α2a using a method such as cation exchange chromatography, anion exchange chromatography, or exclusion chromatography, and then the IFNs-α2a modified by PEG at different single amino acid residues can be further resolved to obtain the YPEG-IFN-α2a in which the YPEG is linked at a specific position. Conventional purification methods include cation exchange chromatography, anion exchange chromatography, hydrophobic interaction chromatography and exclusion chromatography. Characteristic analysis can be performed by a known method in the art, e.g. the mass spectroscopy, the polyacrylamide gel electrophoresis and the high-performance liquid exclusion chromatography can be used to analyze the molecular weight of the products, so as to distinguish the products modified by PEG at a single amino acid residue from those modified by PEG at two or multiple amino acid residues and unmodified IFN-α2a. The above mentioned purification methods can also be used to further resolve the products modified by PEG at a single amino acid residue to obtain different isomers with the PEG modification at different single positions. The in vitro biological activities of all kinds of the PEG modified products can be measured according to any known assay for IFN-activity, e.g. cytopathic effect inhibition. For IFNs modified by PEG at a single amino acid residue, the PEG moieties in the different isomers have different effects on maintaining the active domains of IFNs, resulting in the great differences in the biological activities of different isomers. Generally speaking, the in vitro activities of IFNs are remarkably decreased after PEG modification. However, according to the present invention, the in vitro specific activity of the isolates of three peaks obtained by ion exchange chromatography have been measured, and the results indicate that the isolate of peak 3 (SP2) has significantly higher specific activity than the isolates of other peaks and PEGASYS (Hoffmann-La Roche,

The reaction conditions are mild, the pH is in a range from 4.5 to 9.5, the temperature is between 0-25° C., and stirring or other blending measures are necessary. For detailed conditions please refer to the Examples in DETAILED DESCRIPTION OF THE INVENTION. All YPEGs with different molecular weights can be linked to IFN-α2a using the above method. The products include IFNs-α2a modified at a single amino acid residue (YPEG-IFN-α2a), IFNs-α2a modified at two amino acid residues (YPEG$_2$-IFN-α2a) and IFNs-α2a Basel, Switzerland), and has significantly longer half-life in serum than unmodified IFN-α2a.

In a further embodiment, the Y-branched PEG-linked peptide of the SP2 was sequenced using Edman degradation, and the results showed that the primary component of SP2 was YPEG-IFN-α2a(134).

Hence, in another aspect, the present invention also provides the preparation and purification methods for YPEG-IFN-α2a, comprising:

(a) under an alkaline condition, preferably at pH 9.0, allowing Y-shaped branched PEG as shown in formula (I) below to react with IFN-α2a, and obtaining PEGylated IFN-α2a;

(I)

wherein R and R' are independently a C1-C4 alkyl group, preferably methyl; j is an integer from 1 to 12; m and m' denote the degree of polymerization and can be any integer; and m+m' is preferably from 600 to 1500;

(b) capturing the reaction products in step (a) with an anion exchange resin, preferably Q Sepharose FF, and eluting the products in an anion gradient, preferably in a chloride ion gradient, to obtain modified products;

(c) eluting the reaction products captured in step (b) with a cation exchange resin, preferably SP Sepharose FF, in a cation gradient, preferably in a sodium ion gradient, and collecting each peak separately:

(d) determining the activity of the product from each peak, and selecting the peak corresponding to the reaction product with the highest activity.

DETAILED DESCRIPTION OF THE INVENTION

The present invention will be further described by the following examples, but any example or the combination thereof should not be understood as limiting the scope or embodiment of the invention. The scope of the invention is limited only by the appended claims. In combination with the description and prior art, skilled persons in the art would clearly understand the scope limited by the claims.

Example 1

Preparation of Y-Shaped Branched Peg Modified Recombinant Human IFN-α2a (1) Small-Scale Preparation of Y-Shaped Branched Peg Modified Recombinant human IFN-α2a 166.3 mg of YPEG (formula (I), average molecular weight 40 KD, equal-arm, lot number RD010P041, Beijing JenKem Technology Co., Ltd.) was weighted and dissolved in 1 ml of 2 mM HCl (Guangdong Guanghua Chemical Factory Co., Ltd.). 40 mg of IFN-α2a (Xiamen Amoytop Biotech Co., Ltd.) and 50 mM of boric acid-borax buffer (pH 9.0, Sinopharm Shanghai Chemical Reagent Co., Ltd.) were added to a final reaction volume of 10 ml. In this reaction system, the final concentration of IFN-α2a was 4 mg/ml, and the reaction molar ratio of IFN-α2a and YPEG was 1:2. The reaction system was kept under 0-25° C. for 2 h with stirring. The PEGylated IFNs-α2a were then generated, and the reaction was stopped by adding glacial acetic acid (Shantou Xilong Chemical Co., Ltd.) to make pH<4.0. A sample was subjected for SDS-PAGE. The reaction system was diluted 50 times with water and then 0.2 μm filtered before stored at 4° C. for further use.

Q-Sepharose FF Chromatography was used to separate the remaining PEG and PEG hydrolates, IFNs-α2a modified by YPEG at multiple amino acid residues, IFNs-α2a modified by YPEG at a single amino acid residue and the unmodified IFN-α2a. Q-Sepharose FF (GE Healthcare) column (Φ12 mm×90 mm, 1 CV=10 ml) was regenerated with 3 column volume (CV) of 20 mM boric acid/borax buffer (pH9.0)-1M NaCl (BBI), and then equilibrated with 5 CV of 20 mM boric acid/borax buffer (pH9.0). UV detection wavelength was set at 280 nm. The entire sample stored at 4° C. was loaded. After loading, the column was equilibrated with 3 CV of boric acid/borax buffer (pH9.0), and then 20 mM boric acid/borax buffer (pH9.0)-12 mM NaCl was used for elution until the first peak was completely eluted, which peak was the remaining PEG. 20 mM boric acid/borax buffer (pH9.0)-60 mM NaCl was then used for elution, and the sample collected in this elution peak was primarily the YPEG-IFNs-α2a, modified by PEG at a single amino acid residue. And then 20 mM boric acid/borax buffer (pH9.0)-500 mM NaCl was used for elution and the elution peak was the unmodified IFN-α2a.

The target products were primarily the products modified by PEG at a single amino acid residue, YPEG-IFNs-α2a, with a yield rate of 20-40%.

(2) Large-Scale Preparation of Y-Shaped Branched Peg Modified Recombinant Human IFN-α2a 4989.6 mg of YPEG (formula (I), average molecular weight 40 KD, equal-arm, lot number RD010P041, Beijing JenKem Technology Co., Ltd.) was weighted and dissolved in 25 ml of 2 mM HCl. And 1200 mg of IFN-α2a and 50 mM boric acid/borax buffer (pH 9.0) were added to a final reaction volume of 200 ml. In this reaction system, the final reaction concentration of IFN-α2a was 6 mg/ml, and the reaction molar ratio of IFN-α2a and YPEG was 1:2. The reaction system was kept under 0-25° C. for 2 h with stirring. The reaction was stopped by adding glacial acetic acid to make pH<4.0. A sample was subjected for SDS-PAGE. The reaction system was diluted 50 times with water and then 0.2 μm filtered before stored at 4° C. for further use.

Q-Sepharose FF Chromatography was used to separate the remaining PEG and PEG hydrolates, IFNs-α2a modified by YPEG at multiple amino acid residues, IFNs-α2a modified by YPEG at a single amino acid residue and the unmodified IFN-α2a. Q-Sepharose FF (GE Healthcare) column (Φ38 mm×265 mm, 1 CV=300 ml) was regenerated with 3 CV of 20 mM boric acid/borax buffer (pH9.0)-1M NaCl, and then equilibrated with 5 CV of 20 mM boric acid/borax buffer (pH9.0). UV detection wavelength was set at 280 nm. The entire sample stored at 4° C. was loaded. After loading, the column was equilibrated with 3 CV of 20 mM boric acid/borax buffer (pH9.0), and then 20 mM boric acid/borax buffer (pH9.0)-12 mM NaCl was used for elution until the first peak was completely eluted, which peak was the remaining PEG 20 mM boric acid/borax buffer (pH9.0)-60 mM NaCl was then used for elution, and the sample collected in this elution peak was primarily the YPEG-IFNs-α2a, modified by PEG at a single amino acid residue. And then 20 mM boric acid/borax buffer (pH9.0)-500 mM NaCl was used for elution and the elution peak was the unmodified IFN-α2a.

The target products were primarily the products modified by PEG at a single amino acid residue, YPEG-IFNs-α2a, with a yield rate of 35-50%.

Figure 1:
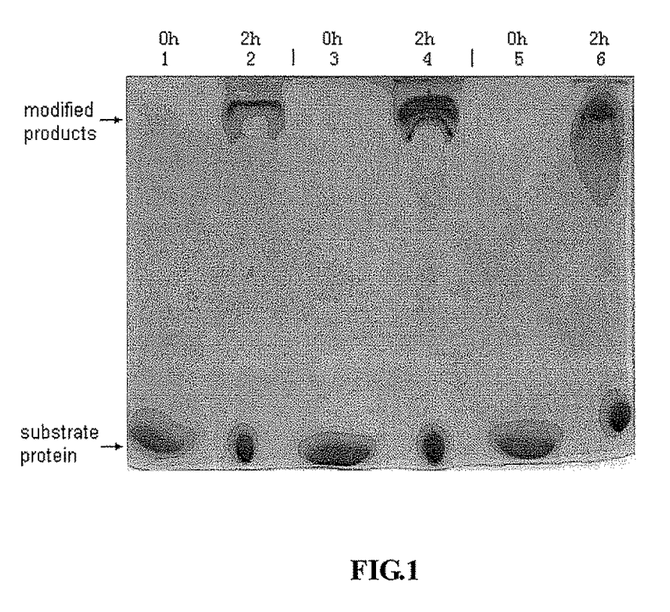
FIG. 1: SDS-PAGE of 3 batches of IFN-α2a modified with YPEG (40 KD). The concentration of the separation gel was 12%, and Coomassie brilliant blue R-250 was used as staining dye. Lanes 1-2: 20060804; Lanes 3-4: 20060807-1; Lanes 5-6: 20060807-2.

FIG. 1 shows SDS-PAGE results for 3 batches of IFNs-α2a modified with YPEG (40 KD). It can be seen from FIG. 1 that under the condition, the PEG modification rate of rhIFN-α2a was between 35-50% and remained stable. The primary modified products were modified by PEG at a single amino acid residue, and there were also some products modified by PEG at multiple amino acid residues.

Example 2

Resolving YPEG-IFNs-α2a by SP-Sepharose FF

Figure 2:
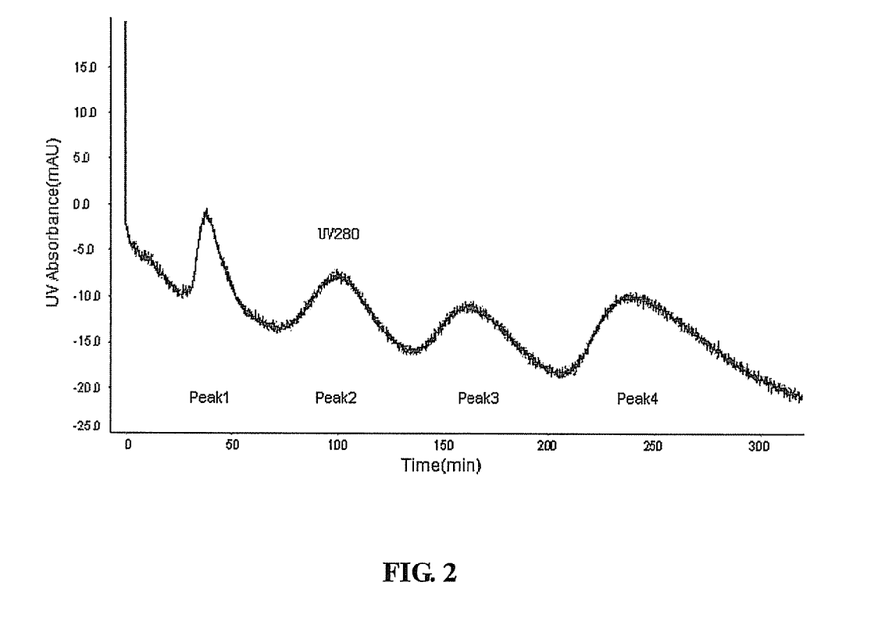
FIG. 2: The resolving profile of YPEG-IFN-α2a modification isomers by SP-Sepharose FF.
Figure 3:
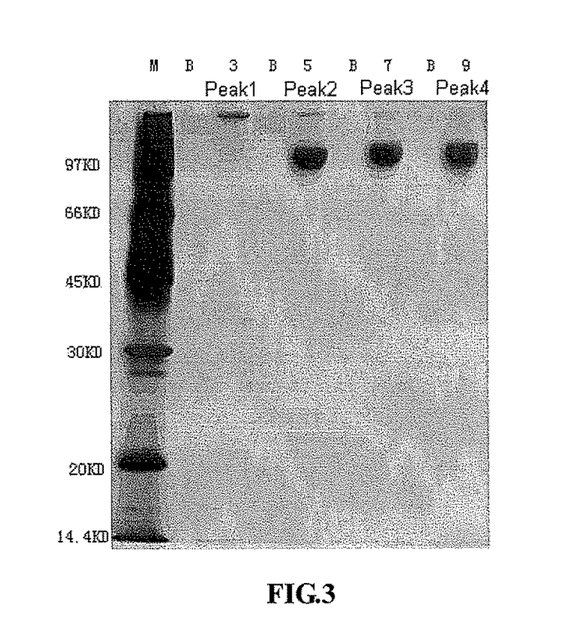
FIG. 3: Silver-stained SDS-PAGE (12%) of the YPEG-IFN-α2a samples purified through SP-Sepharose FF. Lane1: molecular weight marker; Lanes 2, 4, 6, 8, blank; Lanes 3, 5, 7, 9, corresponding respectively to peaks 1 to 4 in the elution profile.

The Q-Sepharose FF captured YPEG-IFN-α2a sample was adjusted to pH 5.0 with 20% acetic acid, then diluted 15 times with 5 mM NaAc/HAc (pH5.0, Shantou Xilong Chemical Co., Ltd.). The sample was loaded at 0.5 mg/ml loading capacity to SP-Sepharose FF 100 ml (GE Healthcare) column (Φ18 mm×394 mm). The column was equilibrated with 3 CV of 5 mM NaAc/HAc (pH5.0), and then eluted with 2.5 CV of the gradient of 0%-30% 5 mM NaAc/HAc-70 mM NaCl (pH5.0), following with 50 CV of the gradient of 30%-100% 5 mM NaAc/HAc-70 mM NaCl (pH5.0). YPEG-IFN-α2a was resolved as 4 elution peaks by SP-Sepharose FF 100 ml. The samples were collected according to these peaks and then tested by SDS-PAGE with silver staining respectively. According to the SDS-PAGE results, it can be seen that peak 1 resolved by SP-Sepharose FF was primarily the products modified by YPEG at multiple amino acid residues (YPEG$_n$-IFN-α2a). Peak 2 by SP-Sepharose FF was primarily the products modified by PEG at a single amino acid residue (YPEG-IFN-α2a), and also contained some products modified by PEG at multiple amino acid residues. Peak 3 and peak 4 by SP-Sepharose FF were both the products modified by PEG at a single amino acid residue. Peaks 2-4 resolved by SP-Sepharose FF were isomers modified with YPEG at different single positions, and were named respectively as YPEG-IFN-α2a SP1, YPEG-IFN-α2a SP2 and YPEG-IFN-α2a SP3. The resolution profile and silver-stained SAD-PAGE results were shown in FIG. 2 and FIG. 3 respectively.

Every sample of YPEG-IFN-α2a SP1-3 was supplemented with sodium chloride, sodium acetate, mannitol, aspartic acid and was sterilized with 0.22 μm filter before stored at 4° C. for further use.

Example 3

Characteristic Analysis of YPEG-IFN-α2a Modification Isomers (1) Protein Concentration by Kjeldahl Method The concentrations of YPEG-IFN-α2a modification isomers were determined by Kjeldahl method.

(2) Protein Apparent Molecular Weight

Figure 4:
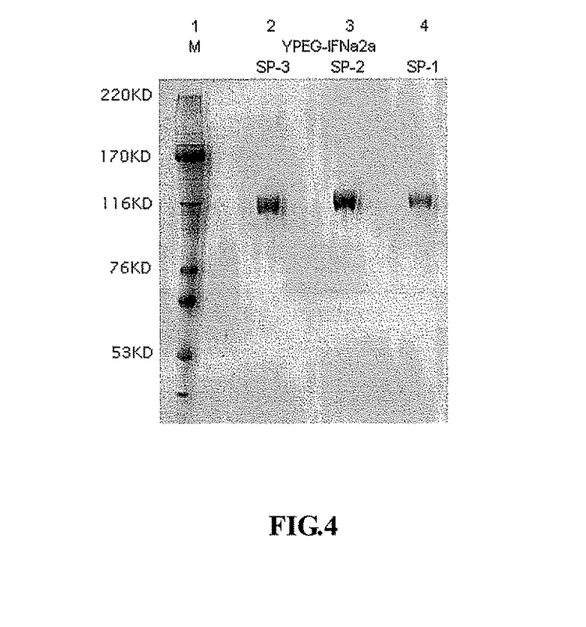
FIG. 4: Apparent molecular weights of the YPEG-IFN-α2a modification isomers in silver-stained SDS-PAGE. Lane 1: molecular weight marker (GE Lifesciences); Lane 2: YPEG-IFN-α2a SP3, 0.4 μg; Lane 3: YPEG-IFN-α2a SP2, 0.4 μg; Lane 4. YPEG-IFN-α2a SP1, 0.4 μg.

The apparent molecular weights of YPEG-IFN-α2a modification isomers were determined by SDS-PAGE. The method was according to Laemmli et al (Nature 227: 680, 1970). The concentration of the gel was 7.5%, and the gel was visualized by silver staining. The apparent molecular weights of YPEG-IFN-α2a modification isomers were almost the same, about 120 KD (FIG. 4).

(3) Molecular Weight Determined by MALDI-TOF MS

Figure 5:
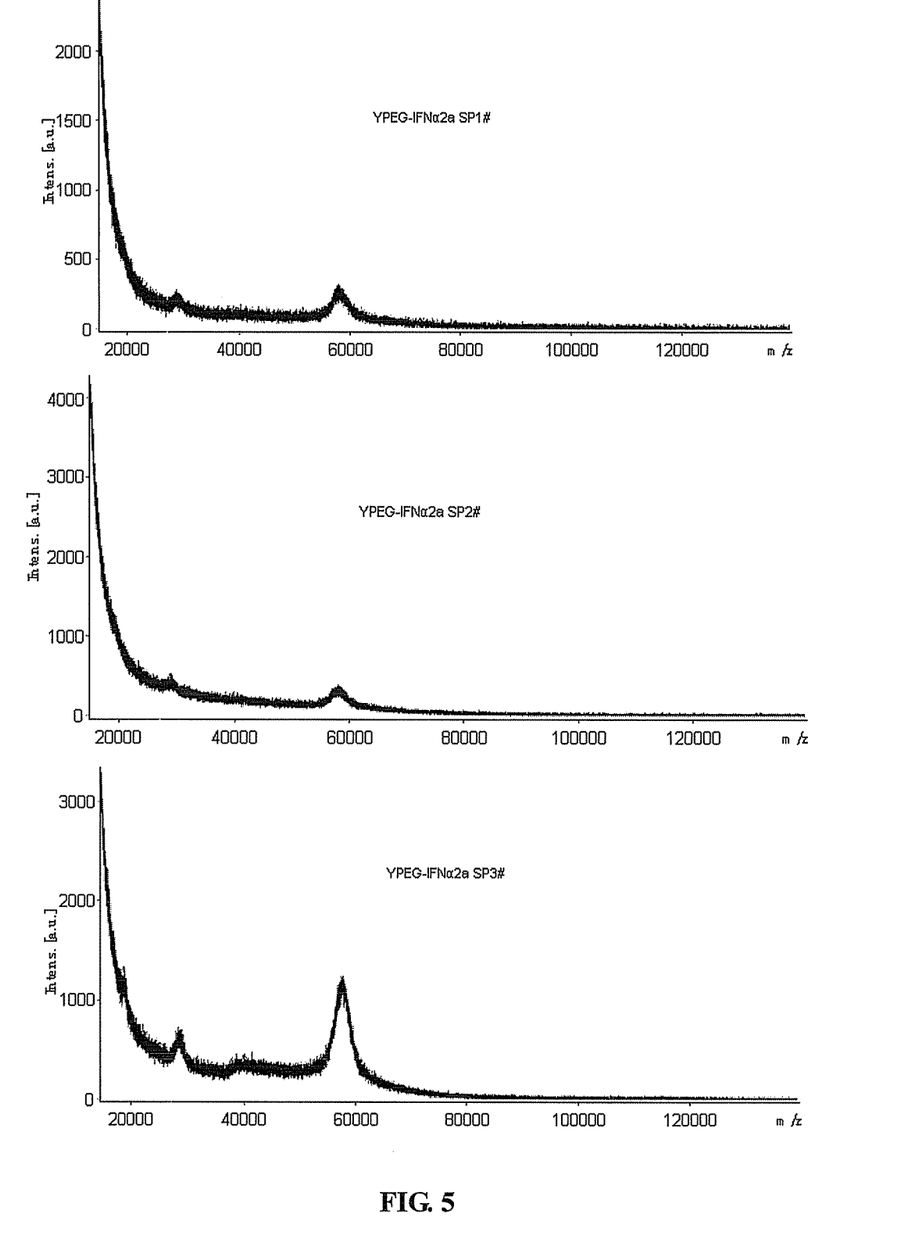
FIG. 5: The molecular weights of the YPEG-IFN-α2a samples purified through SP-Sepharose FF by MALDI-TOF MS. YPEG-IFN-α2a SP1 corresponds to the sample in lane 4 of FIG. 4, YPEG-IFN-α2a SP2 corresponds to the sample in lane 3 of FIG. 4, and YPEG-IFN-α2a SP3 corresponds to the sample in lane 2 of FIG. 4.
Figure 6:
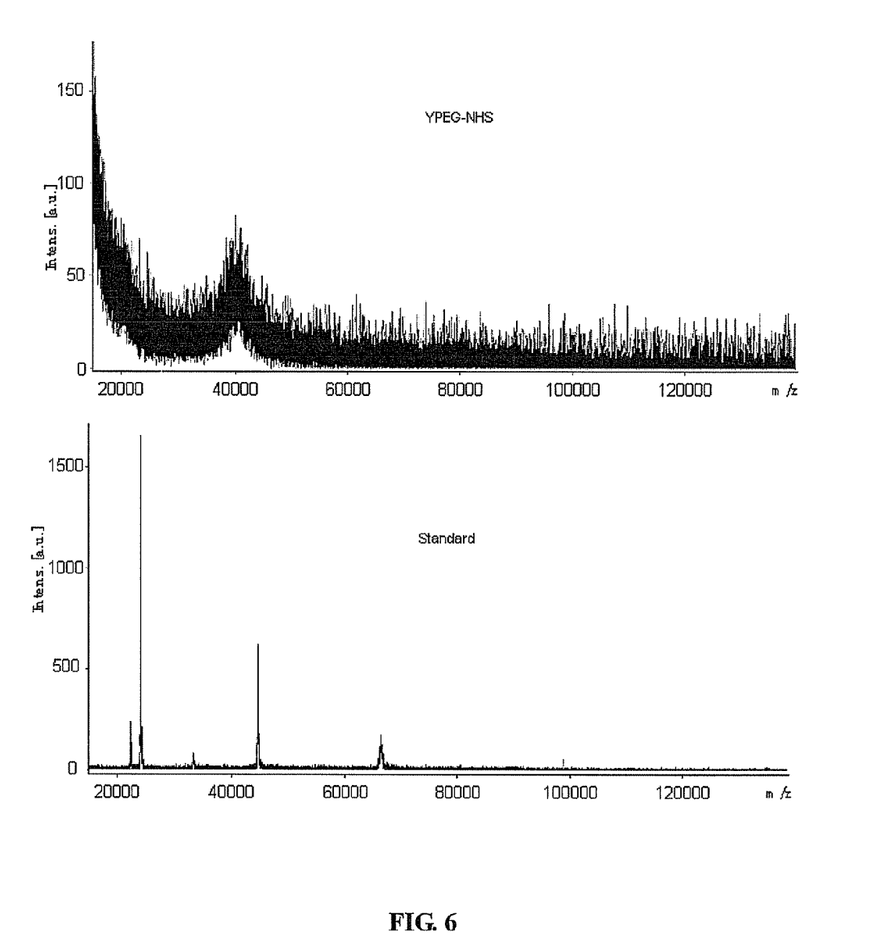
FIG. 6: The molecular weight of YPEG-NHS (40 KD) by MALDI-TOF MS.

MALDI-TOF MS (Autoflex TOF/TOF system, Bruker Daltonics, Germany) was used to determine the molecular weights of YPEG-rHuIFN-α2a modification isomers. Sinapinic acid (SA, $C_{11}H_{12}O_5$, M.W. 224.22, lot number: 2006 236870 002, Bruker Daltonics, Germany) was used as matrix. Protein Calibration Standard II (Part No. 207234, Bruker Daltonics, Germany) was used as protein molecular weight standard, and the software for data analysis was FlexAnalysis Ver.3.0.54.0. The MS molecular weights of YPEG-IFN-α2a modification isomers were almost the same, about 59000 Dalton (FIG. 5).

(4) Protein Purity

The purity of YPEG-IFN-α2a modification isomers was determined by HPLC-SE. HPLC column was TSK G4000 SW$_{XL}$ (Φ7.8 mm×300 mm, TOSOH), the sample loading volume was 20 μl (about 10 μg protein), the mobile phase was 0.1M PBNa-0.1M NaCl (pH7), the flow rate was 0.8 ml/min, and the detection wavelength was set at 280 nm. The YPEG-IFN-α2a SP2 was a single main peak, with a purity more than 99%.

(5) Endotoxin Content Test

Based on *limulus* assay (*Pharmacopoeia of the People's Republic of China*, 2005, Volume 3, Appendix X C), the endotoxin content of every YPEG-IFN-α2a sample was less than 5.0 EU/mg.

(6) In Vivo Activity and Pharmacokinetics of YPEG-IFN-α2a SP2 in Animal.

① In vivo activity of YPEG-IFN-α2a SP2 in animal.

The action mechanism of IFN is partially to induce the production of 2',5'-AS (2',5'-oligoadenylate synthetase), which in turn exerts its antiviral effects. Using $^{125}$I as tracer, the pharmacodynamic parameters of IFN are reflected by the in vivo 2',5'-AS activity. 2',5'-AS catalyzes the synthesis of 2',5'-A (2',5'-oligoadenylate) from ATP in the presence of Poly(I)·Poly(C) agar (The activity of 2',5'-AS can be represented by the concentration of the synthesized 2',5'-A). First, 2',5'-AS in the samples are absorbed and activated by Poly(I)·Poly(C) agarose, then catalyzes the substrate ATP to generate 2',5'-A. A mixture of $^{125}$I labeled 2',5'-A, anti-2',5'-A serum and secondary antibody is added into the sample which then is incubated and centrifugated to separate the mixture. The supernatant is discarded and a Gamma Counter is used to measure the radioactivity of the sediment. The binding rate of the initially added $^{125}$I labeled 2',5'-A is calculated. Four-parameter Logistic regression is used to generate standard curve, and then the concentration of the 2',5'-AS-induced 2',5'-A product in an unknown sample could be estimated.

Figure 7:
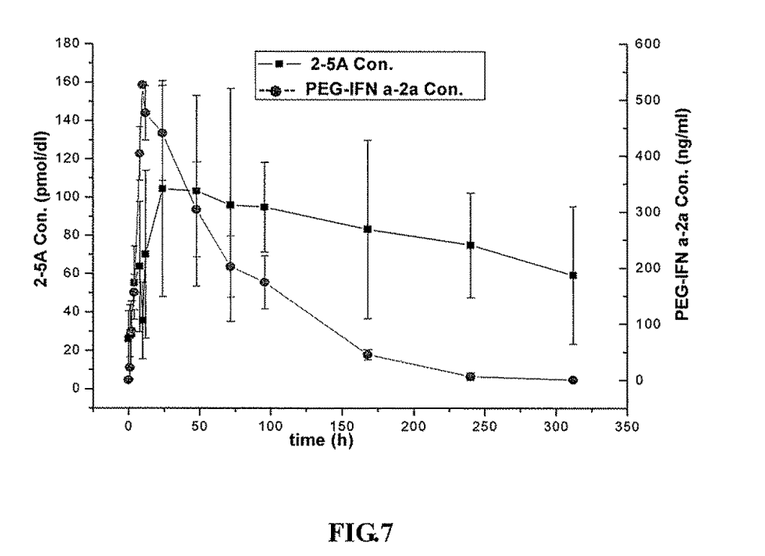
FIG. 7: The serum concentration of the drug and 2', 5'-A concentration after a single s.c. injection of 30 μg·kg$^{-1}$ YPEG-rhIFN-α2a SP2 into Crab-eating Macaque (*Macaca fascicularis*).

Using the above mentioned 2',5'-A method, the results in Table 1 and FIG. 7 showed the serum 2',5'-A concentration after a single s.c. injection of 30 µg·kg$^{-1}$ YPEG-rhIFN-α2a SP2 into Crab-eating Macaque (*Macaca fascicularis*) (15 Crab-eating Macaques, 7 female and 8 male. Laboratory Animal Center of the Academy of Military Medical Sciences, Certification No. SCXK-(MIL)2002-001. Body weight 2.5-3.7 kg, raised in separate cages, fed with standard monkey feed, drink freely). It can be seen from FIG. 5, after administration, the activity of 2',5'-AS in serum was clearly increased, and the time-to-peak of 2',5'-A in serum was delayed than that of YPEG-IFN-α2a SP2. The average time-to-peak was 24±18.33 h, and the concentration to peak was 104.31±56.39 Pmol·dL$^{-1}$.

TABLE 1

The serum 2',5'-A concentrations over time, after a single s.c. injection of 30 µg·kg$^{-1}$ YPEG-rhIFN-α2a SP2 into Crab-eating Macaque. (Pmol · dL$^{-1}$)

| Time (h) | No. of crab-eating Macaque | | | Mean SD |
|---|---|---|---|---|
| | 1 | 2 | 3 | |
| 0 | 16.08 | 19.01 | 42.91 | 26.00 ± 14.72 |
| 1 | 39.04 | — | 16.19 | 27.61 ± 16.16 |
| 2 | 48.21 | 16.90 | 20.20 | 28.44 ± 17.21 |
| 4 | 55.22 | 36.09 | 74.16 | 55.15 ± 19.04 |
| 8 | 32.04 | 59.69 | 99.52 | 63.75 ± 33.92 |
| 10 | 13.52 | 41.21 | 51.85 | 35.53 ± 19.79 |
| 12 | 37.35 | 53.32 | 119.76 | 70.14 ± 43.71 |
| 24 | 58.29 | 167.22 | 87.42 | 104.31 ± 56.39 |
| 48 | 77.50 | 160.67 | 71.41 | 103.19 ± 49.87 |
| 72 | 62.88 | 165.97 | 58.52 | 95.79 ± 60.82 |
| 96 | 73.53 | 119.79 | 90.85 | 94.72 ± 23.37 |
| 168 | 45.41 | 135.26 | 68.92 | 83.20 ± 46.60 |
| 240 | 48.14 | 102.61 | 73.97 | 74.90 ± 27.25 |
| 312 | 93.23 | 21.69 | 62.84 | 59.26 ± 35.90 |

② Pharmacokinetics of YPEG-IFN-α2a SP2 and rhIFN-α2a in Crab-eating Macaque

A single s.c. injection of 7.5, 30 or 120 µg·kg$^{-1}$ YPEG-IFN-α2a SP2 was given to Crab-eating Macaque. For the administration group, 1 ml of venous blood was taken from the hind leg opposite to the injected side at the time before, 1 h, 2 h, 4 h, 8 h, 10 h, 12 h, 24 h, 48 h, 72 h, 96 h, 168 h, 240 h, and 312 h after administration. For the group with a single s.c. injection of rhIFN-α2a (7.5 µg·kg$^{-1}$), 1 ml of blood was taken at the time before, 0.5 h, 1 h, 2 h, 3 h, 4 h, 5 h, 6 h, 8 h, and 24 h after administration. After kept at 4° C. for 30 min, the blood samples were centrifugated at 2000 rpm for 10 min under low temperature, then the serum was separated immediately and stored at −20° C. for further analysis.

The quantitative double sandwich immunoassay was used. A monoclonal antibody specific to the recombinant human IFN-α, was pre-coated on microtiter plate. The standard and the samples were pipetted into the microtiter wells, wherein the rhIFN-α2a or YPEG-IFN-α2a SP2 would bind to the immobilized antibody. The plate was washed to remove unbound substances, and then anti-human IFN-α IgG (secondary antibody) was added into the wells. After the reaction was complete, the plate was washed and the horseradish peroxidase (HRP) was added into the wells. After washing away the unbound enzyme and reagents, the color generated by adding HRP substrate solution into each well was proportional to the amount of the bound IFN-α2a or YPEG-IFN-α2a SP2 in the first step. The reaction was stopped and the color intensity was measured. The higher the OD value of absorbance, the higher the concentration of IFN-α2a or YPEG-IFN-α2a SP2 in the sample. The standard curves were plotted for IFN-α2a and YPEG-IFN-α2a SP2 respectively so as to measure the serum drug concentration in the blood samples.

According to the protocol in the description of the kit (American Biomedical Co., lot number 3271), 100 µl standard or blood sample was added into each well, and mixed with plate mixer gently. According to the anticipated concentration of an unknown sample, the sample was diluted with the dilute solution to the concentration ranges of the standard curve. The rhIFN-α2a or YPEG-IFN-α2a SP2 standard curve for each plate was plotted so as to calculate the concentration of the unknown sample in that plate. The plate was incubated at room temperature for 1 h, and washed once with plate washing solution. 100 µl secondary antibody was added to each well, and kept under room temperature for 1 h. The plate was washed 3 times, and 100 µl HRP conjugate was added to each well. The plate was incubated under room temperature for 1 h and washed 4 times. 100 µl TMB substrate was added into each well, and kept under room temperature in the dark for 15 min. 100 µl stop solution was added to each well, and mixed gently to stop the reaction. The absorbance OD value at 450 nm was measured with a microplate reader within 5 min to determine the concentration of each sample.

After a single s.c. injection of 7.5, 30 or 120 µg·kg$^{-1}$ YPEG-rhIFN-α2a into Crab-eating Macaque, the half-lives were 35.81±2.50, 31.38±11.84 and 36.77±2.24 h, respectively. After a single s.c. injection of 7.5 µg·kg$^{-1}$ rhIFN-α2a into Crab-eating Macaque, the half-life was 3.02±0.55 h. The half-life of rhIFN-α2a was significantly prolonged after PEGylation.

(7) In Vitro Specific Activity

The in vitro biological activity of each YPEG-IFN-α2a modification isomers was estimated using cytopathic effect inhibition assay. According to the method described in *Determination Method of Interferon Activity* (*Pharmacopoeia of the People's Republic of China*, 2005, Volume 3, Appendix X C), interferon protects human amniotic cells (WISH) from the damage caused by vesicular stomatitis virus (VSV). Crystal violet was used to stain survived WISH cells, and the absorbance OD value was measured at 570 nm. The interferon protection effect curve was plotted for WISH cells, so as to determine the in vitro biological activity of interferons. The results of in vitro biological activity of each samples are shown in Table 2, and 3 parallel tests were carried out for each sample. After YPEG modification, in all the modification isomers of the products modified by PEG at a single amino acid residue, the SP2 sample showed the highest in vitro specific activity, which was 1-2 times higher than SP1 and SP3, and also 1-2 times higher than the unresolved sample and PEGASYS (manufactured by Hoffmann-La Roche, Basel, Switzerland; packaged separately by Shanghai Roche Pharmaceuticals Ltd., product lot number B1016, package lot number SH0020).

TABLE 2

In vitro biological activity results for each modification isomer of YPEG-IFN-α2a (3 parallel tests)

| Sample | PEG Type | PEG M.W. (KD) | No. of Modification Positions | Average Specific Activity ($\times 10^6$ IU/mg) |
|---|---|---|---|---|
| YPEG-IFN-α2a SP1 | Y-branched | 40 | 1 | 1.04 ± 0.110 |
| YPEG-IFN-α2a SP2 | Y-branched | 40 | 1 | 2.26 ± 0.129 |
| YPEG-IFN-α2a SP3 | Y-branched | 40 | 1 | 1.11 ± 0.091 |
| YPEG-IFN-α2a unresolved sample | Y-branched | 40 | 1 | 1.01 ± 0.173 |
| PEGASYS | U-branched | 40 | 1 | 0.903 ± 0.056 |

(8) The Resolution of the Modification Position in YPEG-IFN-α2a SP2

The solvent system of YPEG-IFN-α2a SP2 was changed to 50 mM $NH_4HCO_3$ (pH8.0) by ultrafiltration with 5K ultrafilter (Millipore, polyethersulfone material), and the protein concentration was determined to be 4.02 mg/ml using UV spectroscopy. TPCK Trypsin (Promega) was dissolved (0.5 μg/μl) in the solution provided by the manufacturer. Samples were added according to Table 3:

TABLE 3

Reaction composition of YPEG-IFN-α2a SP2 trypsin digestion

| Reaction Components | Volume |
|---|---|
| 50 mM NH4HCO3, pH8.0 | 7.15 ml |
| PEG-IFN-α2a SP2 (4.02 mg/ml) | 1.25 ml |
| Trypsin (0.5 μg/μl) | 0.2 ml |
| Total reaction volume | 8.6 ml |

Figure 8:
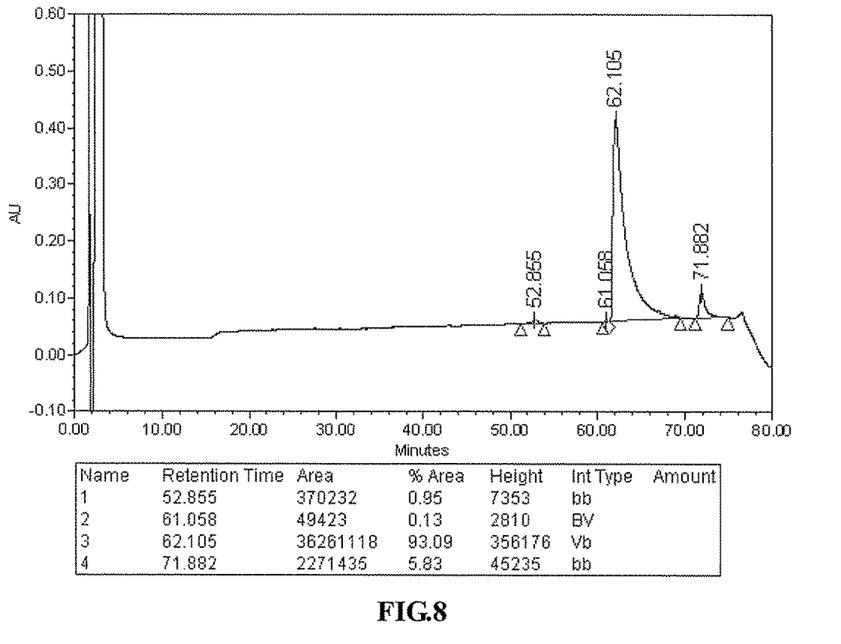
FIG. 8: The analysis of Trypsinase Peptide Mapping of the trypsin digested (0h) YPEG-IFN-α2a SP2 sample by HPLC-RP $C_{18}$. The retention time of YPEG-IFN-α2a SP2 was 62.105 min, the elution peak at 71.882 min was the solvent background, and elution peaks at 2-3 min were trypsin.
Figure 9:
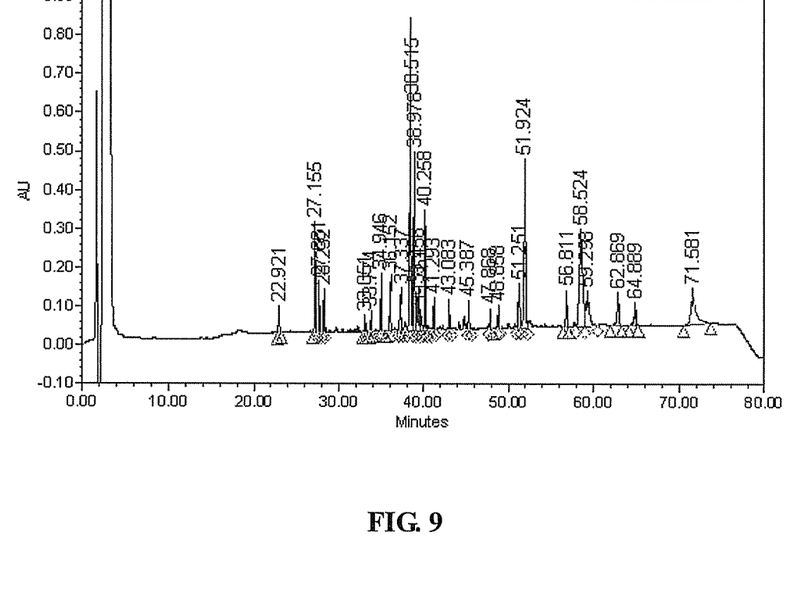
FIG. 9: The analysis of Trypsinase Peptide Mapping of the trypsin digested (48 h) YPEG-IFN-α2a SP2 sample by HPLC-RP $C_{18}$. Solvent peak at 71.581 min was detected, corresponding to the solvent peak at 71.882 min in the trypsin digested (0h) sample. No substrate protein peak (62.105 min) was detected between 59.5 min and 62.5 min, demonstrating the sample was substantially completely digested.

The reaction system was kept in a water bath at 37° C. for 48 h, then 1.52 ml of 20% acetic acid was added to stop the reaction. A small amount of sample was taken for HPLC-RP C18 peptide mapping. The instrument for analysis was Waters HPLC system, with a controller of type 600, 2487 double wavelength detector, and the software for data processing was Empower 2. The HPLC analytical column was Jupiter C18 (particle diameter 5 μm, pore diameter 300 Å, (Φ4.6×150 mm, produced by Phenomenex, USA). Mobile phase A was 0.1% TFA/$H_2O$, Mobile phase B was 0.1% TFA/90% ACN/$H_2O$, the flow rate was 1 mL/min, and the detection wavelength was set at 214 nm. Please refer to Table 4 for the elution gradients, and the results were shown in FIG. 8-9.

TABLE 4

The elution gradients for HPLC-RP C18 peptide mapping of the trypsin digested YPEG-IFN-α2a SP 2

| Time (min) | A % | B % | ACN % |
|---|---|---|---|
| 1 | 0 | 100 | 0 | 0 |
| 2 | 8 | 100 | 0 | 0 |
| 3 | 68 | 40 | 60 | 54 |
| 4 | 72 | 40 | 60 | 54 |
| 5 | 75 | 100 | 0 | 0 |
| 6 | 80 | 100 | 0 | 0 |

Figure 10:
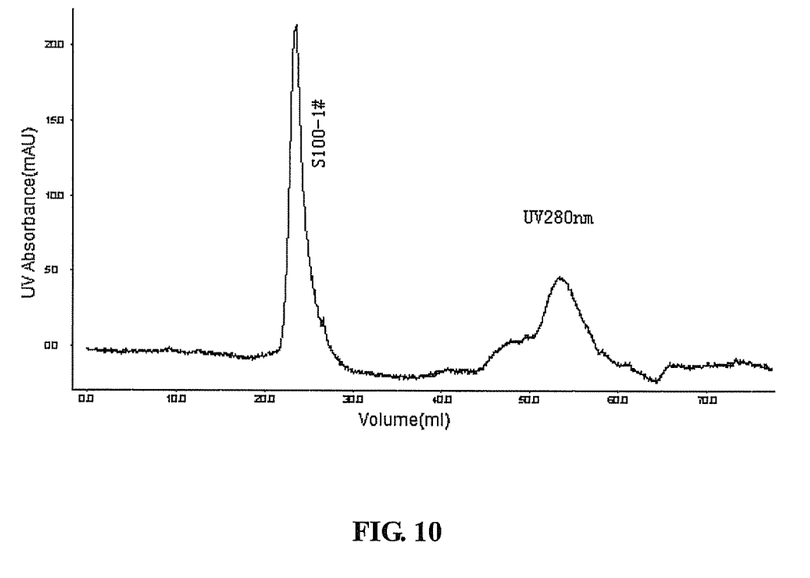
FIG. 10: Sephacryl S-100 HR separation profile of the YPEG modified peptides from the trypsin completely digested YPEG-IFN-α2a SP2 sample.

Based on the detection results, it can be determined that the sample was almost completely digested. The products were treated with DTT reduction after the reaction was stopped. The Sephacryl S-100HR column (Φ18×255 mm, 1 CV-64 ml; GE Healthcare) was pre-equilibrated with 3 CV of 20 mM PBNa-400 mM NaCl (pH7.0), and 3% CV of the YPEG-IFN-α2a SP2 sample by TPCK trypsin digested completely was loaded by hydrostatic pressure. 20 mM PBNa-400 mM NaCl (pH7.0) was used for elution, and the detection wavelength was set at 280 nm. The sample from the first elution peak was collected (sample number: YPEG-IFN-α2a S100-1, FIG. 10), and the solvent system was changed to 5 mM PBNa (pH 7) with 5K ultrafilter. Vacuum freeze-drying was done. The N-terminal amino acids of the freeze-dried sample were determined using Edman degradation, and the sequence of the 7 amino acids at the N-terminus of the sample was XYSPXAW (Table 5), wherein X denotes α-amino acid cysteine (Cys), a non-α-amino acid or another modified amino acid that cannot be detected using Edman degradation. According to the sequence shown in SEQ ID NO: 1, it can be determined that the YPEG-IFN-α2a SP2 was primarily the product modified by YPEG at Lys134.

TABLE 5

Sequencing result for the N-terminal amino acids of YPEG-IFN-α2a S100-1

| Sample | Detected N-terminal Sequence | The corresponding PEG modification position. |
|---|---|---|
| YPEG-IFN-α2a S100-1 | XYSPXAW | Lys134 |

Note:
X denotes α-amino acid cysteine, a non-α-amino acid or another modified amino acid that cannot be detected using Edman degradation.

The invention claimed is:

1. A PEGylated interferon-α2a (IFN-α2a) of the structure as below, obtained by linking IFN-α2a with a Y-shaped branched polyethylene glycol (YPEG):

wherein,
$P_a$ and $P_b$ are same or different polyethylene glycol (PEG);
j is an integer between 1-12;
$R_i$ is H, substituted or unsubstituted C1-C12 alkyl group, substituted aryl, aralkyl, or heteroalkyl; and
$X_1$ and $X_2$ are independently a linking group, wherein $X_1$ is $(CH_2)_n$, and $X_2$ is selected from the group consisting of $(CH_2)_n$, $(CH_2)_n OCO$, $(CH_2)_n NHCO$, and $(CH_2)_n CO$, wherein n is an integer between 1-10, wherein the YPEG is linked to IFN-α2a via an amido bond formed by the side chain ε-amino group of a Lys residue within IFN-α2a corresponding to position 134 in SEQ ID NO: 1.

2. The PEGylated IFN-α2a of claim 1, with the structure as below:

wherein R and R' are independently a C1-C4 alkyl group;
j is an integer between 1-12;
m and m' denote the degree of polymerization and can be any integer; and
the average total molecular weight of the YPEG is from about 10000 to about 60000 Daltons.

3. The PEGylated IFN-α2a of claim 1, wherein the YPEG is an equal-arm YPEG of the molecular weight of 40000 Daltons.

4. The PEGylated IFN-α2a of claim 2, wherein R and R' are independently a methyl group.

5. The PEGylated IFN-α2a of claim 2, wherein m+m' is from 600 to 1500.

6. The PEGylated IFN-α2a of claim 2, wherein the average total molecular weight of the YPEG is about 40000 Daltons.

7. The PEGylated IFN-α2a of claim 2, wherein the IFN-α2a is extracted from a natural source or obtained through recombinant biotechnology.

8. The PEGylated IFN-α2a of claim 7, wherein the IFN-α2a has the amino acid sequence as shown in SEQ ID NO:1.

9. The PEGylated IFN-α2a of claim 7, wherein the IFN-α2a is a recombinant human IFN-α2a.

10. The PEGylated IFN-α2a of claim 7, wherein the recombinant human IFN-α2a is artificially synthesized or expressed from an expression system selected from the group consisting of a prokaryotic expression system, an eukaryotic yeast expression system, an insect cell expression system, and a mammalian cell expression system.

11. The PEGylated IFN-α2a of claim 10, wherein the prokaryotic expression system is *E. coli* cells.

12. The PEGylated IFN-α2a of claim 10, wherein the eukaryotic yeast expression system is *Pichia* cells.

13. The PEGylated IFN-α2a of claim 10, wherein the mammalian cell expression system is CHO cells.

14. A composition comprising a pharmaceutically effective amount of the PEGylated IFN-α2a of claim 1 and a pharmaceutically acceptable carrier or excipient.

15. The composition of claim 14, further comprising mannitol, an amino acid, sodium chloride and sodium acetate.

16. The PEGylated IFN-α2a of claim 15, wherein the amino acid is selected from the group consisting of aspartic acid, asparagine and glycine.

17. A method for preparing and purifying the PEGylated IFN-α2a of claim 1, comprising the steps:

(a) under an alkaline condition, allowing YPEG of the following formula to react with IFN-α2a, and obtaining PEGylated IFN-α2a;

wherein R and R' are independently a C1-C4 alkyl group;
j is an integer between 1-12; m and m' denote the degree of polymerization and can be any integer;
(b) capturing the reaction products obtained in step (a) with an anion exchange resin, and eluting the products in an anion gradient, to obtain modified products;
(c) eluting the reaction products captured in step (b) with a cation exchange resin in a cation gradient, and then collecting each peak separately;
(d) determining the activity of the product from each peak, and selecting the peak corresponding to the reaction product with the highest activity.

18. The method of claim 17, wherein the YPEG has a molecular weight of 40,000 Daltons.

19. The method of claim 17, wherein R and R' are independently a methyl group.

20. the method of claim 17, wherein m+m' is from 600 to 1500.

21. The method of claim 17, wherein pH in step (a) is pH 9.0.

22. The method of claim 17, wherein the anion exchange resin is Q Sepharose FF.

23. The method of claim 17, wherein the anion gradient is a chloride ion gradient.

24. The method of claim 17, wherein the cation exchange resin is SP Sepharose FF.

25. The method of claim 17, wherein the cation gradient is a sodium ion gradient.

26. The method of claim 17, wherein the YPEG is an equal-arm YPEG.

27. The method of claim 17, wherein the IFN-α2a and YPEG are reacted at a molar ratio of 1:2.

28. The method of claim 17, further comprising:
(a) wherein the alkaline condition comprises, at pH 9.0, allowing an equal-arm YPEG of the molecular weight of 40,000 Daltons to react with IFN-α2a, and obtaining PEGylated IFN-α2a; wherein the IFN-α2a and YPEG are reacted at a molar ratio of 1:2; R and R' are independently a C1-C4 alkyl group; j is an integer between 1-12; and m and m' denote the degree of polymerization and can be any integer;
(b) wherein the anion exchange resin is Q Sepharose FF and the anion gradient is a chloride ion gradient; and
(c) wherein the cation exchange resin is SP Sepharose FF and the cation gradient is a sodium ion gradient.

* * * * *

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

-continued

```
Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65              70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100             105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165
```